United States Patent [19]

Goodwin et al.

[11] 4,100,207

[45] Jul. 11, 1978

[54] PREPARATION OF METHYL-SUBSTITUTED PHENOLS

[75] Inventors: Thomas E. Goodwin, College Station, Tex.; Charles M. Starks, Ponca City, Okla.

[73] Assignee: Continental Oil Company, Ponca City, Okla.

[21] Appl. No.: 771,509

[22] Filed: Feb. 24, 1977

[51] Int. Cl.$^2$ ............................................. C07C 39/06
[52] U.S. Cl. ....................................... 568/804; 568/805
[58] Field of Search ............ 260/621 D, 621 R, 624 C

[56] References Cited

U.S. PATENT DOCUMENTS

| 3,296,316 | 7/1967 | Neuworth | 260/621 D |
| 3,346,649 | 10/1967 | Leston | 260/624 C |
| 3,418,380 | 12/1968 | Laufer et al. | 260/624 R |
| 3,470,259 | 9/1969 | Leston | 260/621 D |
| 3,968,172 | 7/1976 | Ichikawa et al. | 260/621 R |
| 3,998,892 | 12/1976 | Leach | 260/624 E |
| 4,041,085 | 8/1977 | Frabetti | 260/621 R |

Primary Examiner—James O. Thomas, Jr.
Assistant Examiner—Werren B. Lone
Attorney, Agent, or Firm—Bayless E. Rutherford, Jr.

[57] ABSTRACT

A method of preparing methyl-substituted phenols is disclosed. The method comprises heating a mixture of mono- or di-hydrocarbyl-substituted cresols and methanol at an elevated temperature in the presence of a catalytic amount of magnesium oxide.

6 Claims, No Drawings

PREPARATION OF METHYL-SUBSTITUTED PHENOLS

GENERAL BACKGROUND

Mono-methyl substituted phenols are known also as cresols. It is well-known that cresols and other methylated phenols are very useful materials. They may be used as resin intermediates, and as solvents for wire enamel. Also, they may be used as intermediates in the preparation of a variety of products such as pesticides, vitamins and nonflammable functional fluids.

It is known that alkylated cresols can be prepared from t-butyl-substituted cresols by two separate and distinct operations, namely debutylation and alkylation. It would be desirable, however, to accomplish this transformation in a single, continuous process. Our invention is directed to such a process (or method).

PRIOR ART

A search of the prior art produced only three references having any possible pertinency to the subject matter of the present invention. These references are U.S. Pat. Nos. 3,296,316; 3,346,649; and 3,470,259. The teachings of these patents are summarized below.

U.S. Pat. No. 3,296,316 teaches alkylation of a mixture of 4-t-butyl-o-cresol and 4-6-di-t-butyl-o-cresol using aluminum phenoxide as the catalyst to produce o-cresol. It also teaches that aluminum phenoxide must be present in the system.

U.S. Pat. No. 3,346,649 teaches a method wherein 4,6-di-t-alkyl-3-lower alkylphenols are dealkylated by heating a 4,6-di-t-alkyl-3-lower alkylphenol in the presence of a catalytic amount of aryloxide of a metal which is zirconium, hafnium, niobium and tantalium. The product is 4-t-alkyl-3-lower phenol.

U.S. Pat. No. 3,470,259 teaches dealkylation of ortho-,para-ditertiary-alkyl-meta-cresols to give meta-cresol by heating the ortho-,para-ditertiary-alkyl-meta-cresols in the presence of a catalytic amount an aryloxide of a metal which is zirconium, niobium, hafnium or tantalium.

Applicants submit that a brief study of the teachings of these references shows that they do not suggest the present invention.

BRIEF SUMMARY OF THE INVENTION

Briefly stated, the present invention is directed to a method of preparing methyl-substituted phenols wherein the method comprises heating a mixture of (a) mono- or di-hydrocarbyl-substituted cresols and (b) methanol at an elevated temperature in the presence of a catalytic amount of magnesium oxide.

In a preferred embodiment the process prepares di- and tri-methyl-substituted phenols.

DETAILED DESCRIPTION

Materials Used

Suitable hydrocarbyl-substituted cresols for use in our process are represented by the formula

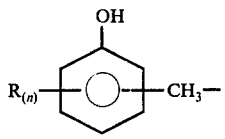

ortho, meta, or para position wherein R is a hydrocarbyl group substituted on any carbon atom other than that attached to the cresylic methyl group. R can be a cyclohexyl, 1-methylcyclohexyl or a $C_4$–$C_6$ tertiary alkyl group, but preferably is a $C_4$–$C_6$ tertiary alkyl group, and n is an integer of 1 or 2. Examples of suitable cresols include the following: 4,6-di-t-butyl-m-cresol, 2,6-di-t-amyl-p-cresol, 4,6-di-t-hexyl-o-cresol, 4-t-butyl-m-cresol, 2-t-amyl-p-cresol, 4,6-di-cyclohexyl-m-cresol, and 2-cyclohexyl-p-cresol.

Our process is restricted to using methanol. In this connection it should be noted that isopropanol does not work in our process.

Suitable amounts of methanol and cresol, expressed as moles alcohol to moles cresol, are in the range of about 0.2:1 to about 15:1. On the same basis, the preferred amounts of alcohol and cresols are in the range of about 0.5:1 to 5:1.

Any commercial grade of magnesium oxide (magnesia) is suitable in our process. Preferably, the magnesium oxide is in the form of small particles, e.g. powder or small granules, pellets, or spheres. Also, preferably, the magnesium oxide is one which can be referred to as "activated". The term "activated" will be better understood from the following discussions. Usually, commercial grades of magnesium oxide are prepared by calcining magnesium carbonate, magnesium hydroxide, or mixtures thereof. Magnesium oxide prepared by calcining at lower temperatures (e.g., below about 1000° C.) are more suitable in that they have lower bulk densities, less periclase material and higher pore volumes. Also, preferably, the activated magnesium oxide will contain from 1 to 5 percent by weight silica since this strengthens the material. Preferably, the activated magnesium oxide will have a pore volume (cc./gram) of 0.1 or higher. More preferably, the pore volume will be 0.5 or higher.

The amount of catalyst is related to the liquid hourly space velocity (LHSV)

$$LHSV = \frac{\text{volume of liquid* per hour}}{\text{volume of catalyst}}$$

*includes both cresol and methanol

A suitable range of LHSV is about 0.1 to 35, with the preferred range being about 0.5 to 9.

Process Conditions

A suitable temperature range for conducting our process is in the range of about 200° to about 575° C. Preferably, the temperature is in the range of about 250° to about 500° C.

The process can be conducted in either vapor or liquid phase. Conducting the process in liquid phase requires sufficient pressure to keep the reactants in the liquid state (usually about 7 to 70 atmospheres).

The reaction time is related to space velocity which has been defined in the foregoing.

While the process can be conducted as a batch operation, preferably it is conducted as a continuous process.

The desired products can be recovered from the reaction admixture by fractional distillation.

While we believe it is understood by those skilled in this art it may be well to note that when t-butylated cresols are used, isobutylene is produced as a by-product. Use of other cresols, as defined hereinbefore, results in the production of the corresponding by-product.

In the description provided herein we have stated both suitable and preferred ranges. It is to be understood that the process is operable using the suitable ranges but that better results can be obtained using the preferred ranges.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the preparation of a mixture of methylated phenols from 4,6-di-t-butyl-m-cresol (DBMC) and methanol. The mole ratio of DBMC:methanol was 1:2. The reaction conditions were:

Temperature = 370° C.
Pressure = 400 psig (28.2 atmospheres)
LHSV = 0.8
Catalyst = activated magnesium oxide powder The isobutylene by-product was collected in a "DRY-ICE"-cooled trap.

The composition of the feedstock and of the reaction product admixture are shown below.

| Component | Area % (by GLC) (3) | |
|---|---|---|
| | Feed | Product |
| m-cresol (1) | — | 5.08 |
| 2,5-xylenol (2) | — | 0.94 |
| 2,3,6-trimethylphenol | — | 0.56 |
| 6-t-butyl-m-cresol | 0.3 | 11.08 |
| 4,6-di-t-butyl-m-cresol | 93.7 | 65.02 |
| unknowns | 5.9 | |

(1) by other nomenclature 2-methyl phenol
(2) by other nomenclature 2,5-dimethyl phenol
(3) closely approximates weight percent

EXAMPLE 2

This example illustrates the preparation of a mixture of methylated phenols from 4,6-di-t-butyl-m-cresol (DBCMC) and methanol, wherein the yield is better than in Example 1. The mole ratio of DBMC:methanol was 1:2. The reaction conditions were:

Temperature = 420° C.
Pressure = 460 psig (32.2 atmospheres)
LHSV = 0.8
Catalyst = activated magnesium oxide powder The isobutylene by-product was collected in a "DRY-ICE"-cooled trap.

The composition of the feedstock and of the reaction product admixture are shown below.

| Component | Area % (by GLC) | |
|---|---|---|
| | Feed | Product |
| m-cresol | — | 8.71 |
| 2,5-xylenol | — | 6.15 |
| 2,3,6-trimethylphenol | — | 2.01 |
| 6-t-butyl-m-cresol | 0.3 | 13.38 |
| 4,6-di-t-butyl-m-cresol | 93.7 | 47.76 |
| unknowns | 5.9 | 21.99 |

Thus, having described the invention in detail, it will be understood by those skilled in the art that certain variations and modifications may be made without departing from the spirit and scope of the invention as defined herein and in the appended claims.

We claim:

1. A method of preparing di- and tri-methyl-substituted phenols wherein the method comprises heating, at a temperature in the range of about 200° to about 575° C., a di-$C_4$-$C_6$-tertiary alkyl cresol and methanol in the presence of a catalytic amount of magnesium oxide, said magnesium oxide being present in an amount in the range of about 0.1 to about 35 expressed as volume of total liquid per hour per volume of catalyst.

2. The method of claim 1 wherein the methanol and di-$C_4$-$C_6$-tertiary alkyl cresol are present in the range of about 0.2:1 to about 15:1, expressed as moles of methanol to di-$C_4$-$C_6$-tertiary alkyl cresol.

3. The method of claim 2 wherein the magnesium oxide is activated magnesium oxide having a pore volume (cc./gram) of 0.1 or higher.

4. The method of claim 3 wherein the hydrocarbyl-substituted cresol is di-t-butyl-m-cresol.

5. The method of claim 4 wherein:
   (a) the temperature is in the range of about 250° to about 500° C.,
   (b) the methanol and cresol feedstock are present in the range of about 0.5:1 to about 5:1, expressed as mole of methanol to cresol, and
   (c) the amount of magnesium oxide catalyst, expressed as volume of total liquid per hour per volume of catalyst, is in the range of about 0.5 to about 9.

6. The method of claim 5 wherein the reaction conditions are:
Temperature = 420° C.
Pressure = 32.2 atmospheres
Catalyst Amount,
LHSV = 0.8

* * * * *